United States Patent
Kubo et al.

(10) Patent No.: US 7,344,771 B2
(45) Date of Patent: Mar. 18, 2008

(54) METHOD FOR SURFACE TREATMENT OF SUBSTRATE, SURFACE-TREATED SUBSTRATE AND DENTAL ARTICLE COMPRISING THE SAME

(75) Inventors: Masao Kubo, Fukushima (JP); Tomohiko Kawasaki, Fukushima (JP)

(73) Assignee: Tomy Incorporated, Fukushima-ken (JP)

( * ) Notice: Subject to any disclaimer, the term of this patent is extended or adjusted under 35 U.S.C. 154(b) by 60 days.

(21) Appl. No.: 10/834,048

(22) Filed: Apr. 29, 2004

(65) Prior Publication Data
US 2004/0219323 A1 Nov. 4, 2004

(30) Foreign Application Priority Data
Apr. 30, 2003 (JP) .......................... P.2003-125998

(51) Int. Cl.
*A61C 8/00* (2006.01)
*B05D 5/10* (2006.01)
*B32B 7/10* (2006.01)
*B32B 27/00* (2006.01)
*B32B 33/00* (2006.01)

(52) U.S. Cl. ................ 428/212; 428/334; 428/339; 428/354; 428/411.1; 427/2.29; 427/299; 433/201.1

(58) Field of Classification Search ................ 428/212, 428/411.1, 522, 334, 339, 354; 427/2.26, 427/2.29, 299; 433/199.1, 201.1
See application file for complete search history.

(56) References Cited

U.S. PATENT DOCUMENTS

| 2,472,492 | A | * | 6/1949 | Saffir ........................... 156/61 |
| 3,628,987 | A | * | 12/1971 | Nakata et al. .............. 428/353 |
| 4,595,364 | A | * | 6/1986 | Kusano et al. .............. 433/185 |
| 4,634,381 | A | * | 1/1987 | Kusano et al. .............. 433/172 |
| 5,418,262 | A |   | 5/1995 | Gobel |
| 5,558,516 | A | * | 9/1996 | Horn et al. .................... 433/9 |

FOREIGN PATENT DOCUMENTS

| JP | 6-285087 A | | 10/1994 |
| JP | 10-248857 A | | 9/1998 |
| JP | 2000-93436 A | | 4/2000 |
| JP | 2001089693 A | * | 4/2001 |
| WO | WO 97/00922 A1 | | 1/1997 |

OTHER PUBLICATIONS

English language translation of Hatanaka, JP 2001-089693 A, Apr. 2001.*
Database WPI, Section Ch, Week 200316 Derwent Publications Ltd., London, GB; Class A13, AN 2003-159848, XP002292380 & Japanese Abstract 2002245667, dated Aug. 30, 2002.

* cited by examiner

*Primary Examiner*—Ramsey Zacharia
(74) *Attorney, Agent, or Firm*—Sughrue Mion, PLLC

(57) ABSTRACT

A method for a surface treatment of a substrate comprises providing a protective layer having a solubility parameter different from that of an adhesive by 1 or less on an bonding surface of a substrate before bonding the substrate with the adhesive.

3 Claims, No Drawings

METHOD FOR SURFACE TREATMENT OF SUBSTRATE, SURFACE-TREATED SUBSTRATE AND DENTAL ARTICLE COMPRISING THE SAME

BACKGROUND OF THE INVENTION

1. Field of the Invention

The present invention relates to a method for a surface treatment of a substrate, a substrate thus surface-treated and a dental article comprising a substrate. More specially, the present invention relates to a method for a surface treatment of a substrate such as ceramics, plastic and metal and a substrate surface-treated and more particularly to a method for a surface treatment of a dental article for use in dental treatment including prosthesis such as a metallic crown or denture and orthodontic treatment.

2. Description of the Related Art

In general, in order to bond a substrate such as ceramics, plastic and metal with using an adhesive, it is practiced to subject the substrate to surface treatment for enhancing the adhesive property thereof. Methods for the surface treatment of a substrate can be roughly divided into two known groups, i.e., dry treatment and wet treatment.

Known examples of dry treatment include blasting, flame treatment, corona discharge treatment, plasma treatment, ultraviolet treatment, laser irradiation treatment, and ozone oxidation. Known examples of wet treatment include treatment with coupling agent, and primer coating.

For example, a ceramics substrate to be used in the dental article for dental treatment, circuit board, glass for liquid crystal, photomask, etc. is often subjected to plasma treatment, ultraviolet treatment or the like so that organic materials and other materials on the surface thereof are decomposed away to improve the adhesive property thereof (see, e.g., JP-A-10-248857).

It is also known that such a ceramics substrate is subjected to blasting (method which comprises allowing an abrasive to collide with the surface of the object in the stream of pressurized air to remove foreign matters from the surface of the object) or the like so that the surface of the ceramics substrate is roughened to enhance the adhesive property thereof (see, e.g., JP-A-6-285087).

It is also often practiced particularly in the art of dentistry to subject the surface of a dental article for dental treatment to primer coating with a compound normally made of an aromatic carboxylic acid or the like called primer. In this manner, a protective layer is formed on the surface of the dental article for dental treatment, making it possible to enhance the adhesive property of the article or stabilize the surface conditions of the article (see, e.g., JP-A-2000-93436).

However, the ceramics substrate which has thus been subjected to surface treatment can adsorb organic materials and thus lose its adhesive strength with time when it is left unbonded even if organic materials have been removed by plasma treatment or ultraviolet treatment.

Further, even the substrate which has been subjected to blasting can adsorb a polar compound or the like by the area where hydroxyl groups are exposed and thus lose its surface adhesive strength when it is left untreated.

Moreover, in the case where the substrate is subjected to primer coating to form a protective layer on the bonding surface thereof, the protective layer deteriorates after prolonged storage, making it likely that the adhesive strength of the substrate can be deteriorated.

Therefore, the surface treatment, if effected for the purpose of enhancing adhesive property, needs to be effected shortly before bonding. However, it is troublesome to effect the surface treatment shortly before bonding of the substrate. Similar problems occur not only with ceramics substrates but also with plastic substrates and metallic substrates.

SUMMARY OF THE INVENTION

An object of the invention is to provide a surface treatment method which can prevent the drop of the adhesive strength of the surface of a substrate made of ceramics, plastic, metal or the like even after prolonged storage.

The invention uses the following means as a technical constitution for accomplishing the aforementioned object.

In other words, a method for a surface treatment of a first aspect of the invention comprises providing a protective layer having a solubility parameter different from that of an adhesive by 1 or less on the bonding surface of a substrate before bonding the substrate with the adhesive.

In accordance with the aforementioned surface treatment method, the formation of a protective layer on the bonding surface of the substrate makes it possible to prevent foreign matters capable of lowering adhesive strength from being adsorbed on the bonding surface of the substrate. Further, by making the difference in solubility parameter between the protective layer and the adhesive for bonding the substrate as small as 1 or less, the component of the protective layer and the adhesive can be rendered more soluble in each other, making it possible to bond the adhesive to the bonding surface of the substrate with a high adhesive strength. Accordingly, the drop of the adhesive strength of the substrate can be prevented even after prolonged storage.

According to a second aspect of the invention, the method for the surface treatment of the invention is also characterized in that the protective layer is made of an organic polymer compound.

In accordance with the aforementioned surface treatment method, the protective layer is made of an organic polymer compound. Thus, the protective layer can be more easily formed by a coating method or the like.

According to a third aspect of the invention, the method for the surface treatment of the invention is further characterized in that the bonding surface of the substrate is subjected to pretreatment before the formation of the protective layer.

In accordance with the aforementioned surface treatment method, the bonding surface of the substrate is subjected to pretreatment, making it possible to further enhance the adhesive strength between the substrate and the adhesive.

The substrate of a fourth aspect of the invention is subjected to surface treatment by a method according to any of the first to third aspect of the invention.

In this arrangement, a substrate which is little subject to drop of surface adhesive strength even after prolonged storage can be provided.

The dental article for dental treatment of a fifth aspect of the invention is made of a substrate according to the fourth aspect of the invention.

In this arrangement, a dental article for dental treatment which is little subject to drop of surface adhesive strength even after prolonged storage can be provided.

DETAILED DESCRIPTION OF THE INVENTION

The substrate to be used in the method for the surface treatment of the invention is not specifically limited but may be a ceramic, plastic, metal or the like. The substrate to be used herein may be a composite of these materials.

As the ceramic there may be used any of various ceramic materials for use in the art of precision machine, semiconductor, medical treatment, etc. Specific examples of these ceramic materials include alumina ceramics, glass ceramics, silicon carbide-based ceramics, and silicon nitride-based ceramics. The ceramic substrate according to the invention can be produced by an ordinary sintering method or the like.

The plastic may be a thermoplastic or thermosetting resin. Specific examples of the thermoplastic resin employable herein include polyethylene, vinyl chloride resin, and nylon. Specific examples of the thermosetting resin include phenolic resin, epoxy resin, and urethane resin.

The plastic may comprise an oxidation inhibitor, a stabilizer, a nucleating agent, an antistatic agent or other various commonly used additives included therein. The plastic substrate according to the invention can be produced by an ordinary molding method or the like.

The metal to be used herein is not specifically limited but may be a in the form of simple substance or compound such as oxide and carbonate. In some detail, a stainless steel or the like may be used. The metallic substrate according to the invention can be produced by an ordinary casting method or the like.

The method for the surface treatment of the invention involves the formation of a protective layer on the bonding surface of the aforementioned substrate. The material of the protective layer is selected such that the difference in solubility parameter between the protective layer and the adhesive for bonding the substrate is 1 or less.

The material to be used as the protective layer of the invention maybe any of organic compounds, inorganic compounds, etc. or may be a low molecular compound or polymer compound. The material of the protective layer may be a single compound or a mixture of compounds.

The protective layer is preferably made of the organic polymer compound among the aforementioned compounds. The organic polymer compound, if used, preferably has a molecular weight of from 10,000 to 100,000 from the standpoint of volatility, stability, etc. Specific examples of the material of the protective layer employable herein include thermosetting epoxy resins, thermosetting phenolic resins, polyvinyl acetates, and ethylene-vinyl acetate copolymers.

The solubility parameter (SP value) of the protective layer according to the invention can be determined by the following equation (1) if the protective layer is made of a low molecular compound:

$$\delta_1 = (\Delta E_1/V_1)^{1/2} \quad (1)$$

wherein $\delta_1$ is the solubility parameter; $\Delta E_1$ is the vaporization energy of the compound constituting the protective layer at 25° C.; and $V_1$ is the molar volume of the compound constituting the protective layer calculated from the molecular weight and density thereof.

The solubility parameter (SP value) of the protective layer according to the invention can be determined by the following equation (2) according to Fedors' method (see "Polymer Engineering and Science", 1974, Vol. 4, No. 2) if the protective layer is made of a polymer compound:

$$\delta_2 = (\Sigma \Delta E_2/\Sigma \Delta V_2)^{1/2} \quad (2)$$

wherein $\delta_2$ is the solubility parameter; $\Delta E_2$ is the vaporization energy of the atoms or atomic groups contained in the compound constituting the protective layer; and $\Delta V_2$ is the molar volume of the atoms or atomic groups contained in the compound constituting the protective layer. The solubility parameter of the polymer compound to be used in the protective layer is calculated from $\Delta E_2$ and $\Delta V_2$ value of the various atoms or atomic groups described in the above cited literature.

If the protective layer comprises a plurality of compounds, the solubility parameter of the protective layer can be determined by the solubility parameter of the various compounds calculated by the aforementioned equation (1) or (2) and the content of the various compounds.

By providing such a protective layer, the surface of the substrate can be protected, making it possible to prevent foreign matters capable of lowering adhesive strength from being attached to the surface of the substrate. In addition, the surface of the substrate can be stabilized or rendered corrosion-resistant or adhesive.

Further, by selecting the material of the protective layer such that the difference in SP value between the protective layer and the adhesive for use in the bonding of the substrate is as small as 1 or less (preferably 0.5 or less), the protective layer and the adhesive layer can be rendered more soluble in each other when the adhesive is applied over the bonding surface of the substrate. Accordingly, the adhesive and the protective layer can be firmly bonded to each other by a chemical bond, making it possible to prevent the drop of adhesive strength of the substrate even after prolonged storage.

The thickness of the protective layer may be such that the function of the surface of the substrate is not impaired. In some detail, the thickness of the protective layer is preferably from 10 μm to 100 μm. When the thickness of the protective layer exceeds 100 μm even if SP value of the protective layer is close to that of the adhesive, it takes much time for the adhesive and the protective layer to undergo mutual dissolution, occasionally making it impossible to obtain a desired adhesive strength.

In order to provide a protective layer on the surface of the substrate, the aforementioned compounds may be applied over the surface of the substrate in the form of solution in a solvent such as acetone and dichloromethane, and then dried.

The time at which the protective layer is provided is not specifically limited so far as it is before the application of the adhesive but is preferably before the prolonged storage of the substrate. In the case where pretreatment is effected to improve the adhesive strength as described later, the protective layer is preferably formed shortly after the pretreatment.

In the surface treatment of the invention, pretreatment is preferably effected before the provision of the protective layer for the purpose of enhancing adhesive property and cleaning, stabilizing and protecting the bonding surface of the substrate. As such pretreatment there may be effected any of primer coating, mechanical treatment, chemical treatment and physical treatment. Two or more of these pretreatments may be effected in combination. These pretreatments may be properly selected depending on the application of the substrate.

In some detail, as the primer to be used in primer coating there may be used 4-methacryloyloxycarbonylphthalic acid or the like. As the mechanical treatment there may be used sand blasting treatment or the like. Alternatively, the bonding surface of the substrate may be abraded with a polishing paper, wire brush or the like.

As the chemical treatment there may be used a silane coupling or the like. As the physical treatment there may be used ultraviolet treatment, laser irradiation, corona discharge, flame treatment, ozone oxidation or the like.

By effecting such a treatment before the formation of the protective layer, the bonding surface of the substrate can be modified, making it possible to enhance the mechanical bond (bond by anchoring effect) of the substrate to the adhesive, the physical interaction (electrical bond or the like) or the chemical interaction and hence the bond strength with respect to the adhesive. Further, the bonding surface of the substrate can be cleaned or stabilized or freed of foreign matters such as oil, water, rust and dust. Accordingly, the substrate can be more firmly bonded to the object.

The substrate which has been subjected to surface treatment according to the invention can be pressure-bonded to another substrate with an adhesive applied over the protective layer.

During the bonding of the substrate which has been subjected to surface treatment according to the invention to another substrate with an adhesive, the protective layer and the adhesive may be dissolved in each other and mixed with each other, giving an indefinite border of the protective layer with the adhesive after bonding. Some combinations of the protective layer and the adhesive may involve complete dissolution of the protective layer in the adhesive. In this case, only adhesive layer is present between the substrate and another substrate thus bonded. Alternatively, in the case where the aforementioned pretreatment has caused the formation of a thin layer, only the thin layer and the adhesive layer may be present.

The adhesive to be used in the surface treatment of the invention is not specifically limited but may be properly selected depending on the purpose. Specific examples of the adhesive employable herein include Accubond (two-paste type, chemically-polymerized, commercially available from GAC International, Inc. of US).

The surface treatment method of the invention can be applied to substrates for all purposes. For example, automobile, building, circuit board, articles for medical treatment, etc. can be used as a substrate. Among the articles for medical treatment, members for use in dental treatment including prosthesis such as a metallic crown or denture and orthodontic treatment are preferably used as a substrate.

Examples of dental articles for use in dental treatment which can be used as a substrate include orthodontic appliances requiring adhesion (e.g., bracket, band, buccal tube), denture, and denture base for fixing denture. These articles are normally formed by ceramics, metal, plastic, etc.

The surface treatment of orthodontic bracket as an example of dental article will be described hereinafter.

An orthodontic bracket is one of dental articles most frequently used for correction of irregularities of the teeth and is normally bonded to the teeth. In general, the bonding surface of such a bracket with the teeth has an unevenness provided thereon for increasing the bonding area with the teeth. As such an orthodontic bracket there is well known one made of ceramics, metal, plastic or composite thereof.

The bonding surface of the orthodontic bracket is normally subjected to pretreatment such as the aforementioned primer coating, sandblasting, silane coupling and corona discharge treatment to further enhance its adhesive property. The bonding surface thus treated can be subjected to deterioration of function (drop of adhesive strength) when it is left untreated unless the bracket is bonded to the teeth shortly after the pretreatment.

However, in accordance with the surface treatment method of the invention, a protective layer having SP value different from that of the adhesive used for the orthodontic bracket by 1 or less is formed on the bonding surface of the orthodontic bracket, making it possible to prevent foreign matters from being attached to the bonding surface of the bracket even after prolonged storage. Further, when the orthodontic bracket is bonded to the teeth, the protective layer and the adhesive are dissolved in each other, making it possible to prevent the drop of adhesive strength of the bracket to the teeth.

More particularly, in the case where the orthodontic bracket is bonded to the teeth with an acrylic adhesive (e.g., Accubond; SP value: 9.0 to 9.4), a dilute solution (1 to 3%) of a polyvinyl acetate or ethylene-vinyl acetate (SP value: 8.8 to 9.4) in a volatile solvent (e.g., dichloromethane, chloroform, acetone) is applied over the bracket which has been subjected to pretreatment for enhancing adhesive property (e.g., blasting) to a thickness of from 10 µm to 30 µm, and then dried to provide a protective layer.

By making the difference in SP value between the adhesive used and the component of the protective layer 1 or less, the protective layer provided on the bonding surface of the bracket can be mutually dissolved with and easily integrated to the adhesive when the bracket is bonded to the teeth.

While the aforementioned embodiment has been described with reference to the case where an acrylic adhesive is used, the adhesive to be used is not specifically limited so far as it can be used for the orthodontic bracket. The kind and concentration of the compound to be used in the protective layer and the solvent to be used therefore are not specifically limited, but the protective layer is preferably made of a polymer compound.

The method for applying the coating solution of the component of the protective layer over the bonding surface of the bracket is not specifically limited. Examples of the applying method employable herein include dipping, spraying, and brushing.

While the invention has been described with reference to the case where as the substrate according to the present embodiment of implementation of the invention there is used a orthodontic bracket, which is one of dental article, the method for the surface treatment of the invention is not limited to the orthodontic bracket but may be applied to other orthodontic appliances (e.g., band, buccal tube) or other articles requiring adhesion to the teeth or other articles such as denture and denture base.

EXAMPLE

The invention will be further described in the following examples and comparative examples, but the invention should not be construed as being limited thereto.

[Sample 1]

An alumina ceramics bracket (tradename: Crystaline® IV; external dimensions: 3 mm×4 mm×2 mm; manufactured by TOMY Inc.) was subjected to sandblasting with #150 silicon carbite abrasives on the bonding surface thereof using a wet type blasting machine produced by Abrasion Development Inc. of England.

[Sample 2]

The alumina ceramics bracket of Sample 1 was coated with a 1% solution of a thermosetting epoxy resin (SP value: 11.5; trade name: MARKEM 2424, produced by MARKEM CORPORATION OF US) in dichloromethane on the blasted surface thereof shortly after being blasted, and then dried at 80° C. for 30 minutes to form a protective layer thereon. The thickness of the protective layer thus formed was 30 µm.

[Sample 3]

The procedure of Sample 2 was followed except that a thermosetting phenolic resin (SP value: 11.0; trade name:

MARKEM 2471, produced by MARKEM CORPORATION OF US) was used instead of the thermosetting epoxy resin.

[Sample 4]

The procedure of Sample 2 was followed except that a polyvinyl acetate (SP value: 9.4; commercially available from Kanto Kagaku) was used instead of the thermosetting epoxy resin.

[Sample 5]

The procedure of Sample 2 was followed except that a ethylene-vinyl acetate copolymer (SP value: 8.9; commercially available from Kanto Kagaku) was used instead of the thermosetting epoxy resin.

[Sample 6]

The procedure of Sample 1 was followed except that blasting was replaced by silane coupling which comprises spray-applying a silane coupling agent (trade name: LS-3380, produced by Shin-Etsu Chemical Co., Ltd.) diluted with methanol (concentration of silane coupling agent: 1% by weight) over the bonding surface of the alumina ceramics bracket, and then heating the bracket to 120° C. for 1 hour.

[Sample 7]

The procedure of Sample 6 was followed except that a protective layer was formed in the same manner as in the procedure of Sample 4 shortly after silane coupling.

[Sample 8]

A polycarbonate (trade name: Lexan, produced by GE Plastics Inc.) was molded to the same shape as that of Sample 1. The molded product was then irradiated on its bonding surface with ultraviolet rays from a type TOSCURE HC-411 high voltage mercury vapor lamp (400 W, produced by Toshiba Corporation) disposed at a distance of 20 cm therefrom.

[Sample 9]

The procedure of Sample 8 was followed except that a protective layer was formed in the same manner as in the procedure of Sample 4 shortly after irradiation with ultraviolet rays.

Two sets were prepared for each of Samples 1 to 9. One of the two sets was coated with a chemically-polymerized acrylic adhesive (SP value: 9.2; trade name: Accubond, produced by GAC International, Inc. of US), and then bonded to an adherend (silane-treated alumina ceramic in the form of cylinder having a diameter of 8 mm and a height of 10 mm).

Samples 1 to 9 thus prepared were each then measured for shearing adhesive strength using a Type 5567 tensile testing machine (produced by Instron Corporation of US).

The measurements are set forth in Table 1 below.

TABLE 1

| Sample No. | SP value of protective layer[Note 1] | Adhesive strength measured shortly after preparation (kgf) | Adhesive strength measured after 4 weeks of storage (kgf)[Note 2] | Inventive/comparative |
|---|---|---|---|---|
| Sample 1 | — (—) | 17 | 7.7 (45.3%) | Comparative |
| Sample 2 | 11.5 (2.3) | 11 | 5.7 (51.8%) | Comparative |
| Sample 3 | 11.0 (1.8) | 14 | 7.5 (53.6%) | Comparative |
| Sample 4 | 9.4 (0.2) | 14 | 10.5 (75.0%) | Inventive |
| Sample 5 | 8.9 (0.3) | 13 | 9.7 (74.6%) | Inventive |
| Sample 6 | — (—) | 22 | 8.6 (39.1%) | Comparative |
| Sample 7 | 9.4 (0.2) | 17 | 12.4 (72.9%) | Inventive |
| Sample 8 | — (—) | 16 | 8.1 (50.6%) | Comparative |
| Sample 9 | 9.4 (0.2) | 15 | 9.8 (65.3%) | Inventive |

[Note 1] The figure in the parentheses indicates the difference (absolute value) of SP value from that (9.2) of the adhesive used in the present example.
[Note 2] The figure in the parentheses indicates the percent retention from the initial adhesive strength of the sample ((adhesive strength after 4 weeks)/(adhesive strength shortly after preparation) × 100 (%)).

As can be seen in the aforementioned results, the comparison of the samples of the invention with the comparative samples comprising the same substrate as the samples of the invention show that the substrate comprising a protective layer of the invention (samples 4, 5, 7, 9) has an extremely great retention of adhesive strength after 4 weeks as compared with the comparative examples (samples 1 to 3, 6, 8).

In accordance with the invention, the bonding surface of a substrate made of ceramics, plastic, metal or the like comprises a protective layer having a high compatibility with an adhesive provided thereon, making it possible to prevent the adhesive strength of the substrate from decreasing even after prolonged storage.

What is claimed is:

1. A method for a surface treatment of a substrate, said method comprising:
    subjecting a bonding surface of the substract to pretreatment:
    providing a protective layer, having a solubility parameter different from that of an adhesive by 1 or less, on the pretreated bonding surface of the substrate before bonding the substrate with the adhesive; and
    bonding the substrate with the adhesive,
    wherein the protective layer is made of an organic polymer compound and has a thickness of 10-100 μm.

2. A substrate which has been subjected to a surface treatment by a method comprising providing a protective layer, having a solubility parameter different from that of an adhesive by 1 or less, on a bonding surface of the substrate before bonding the substrate with the adhesive, and bonding the substrate with the adhesive, wherein the protective layer is made of an organic polymer compound and has a thickness of 10-100 μm, wherein the bonding surface of the substrate is subjected to pretreatment before the formation of the protective layer.

3. A dental article comprising:
    a bonding surface;
    a protective layer provided on said bonding surface of said dental article; and
    an adhesive provided on said bonding layer, for adhering said dental article to a tooth,
    wherein said protective layer has a solubility parameter different from that of said adhesive by 1 or less and has a thickness of 10-100 μm,
    wherein said bonding surface of said dental article is a pre-treated surface, and wherein said protective layer is provided on said pre-treated surface.

* * * * *